United States Patent
Andrews et al.

(10) Patent No.: US 6,592,576 B2
(45) Date of Patent: Jul. 15, 2003

(54) MYOCARDIAL REVASCULARIZATION

(75) Inventors: Robert R. Andrews, Norfolk, MA (US); Robert I. Rudko, Holliston, MA (US); Richard P. Yeomans, Jr., Medway, MA (US); Italo J. DeSantis, Medway, MA (US); Weslaw Gronek, Northbridge, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 0 days.

(21) Appl. No.: 09/867,349

(22) Filed: May 29, 2001

(65) Prior Publication Data

US 2002/0032437 A1 Mar. 14, 2002

Related U.S. Application Data

(62) Division of application No. 09/519,502, filed on Mar. 6, 2000, now Pat. No. 6,464,693.

(51) Int. Cl.[7] .............................................. A61B 18/18
(52) U.S. Cl. ................................ 606/15; 606/1; 606/10
(58) Field of Search ...................................... 606/10–17

(56) References Cited

U.S. PATENT DOCUMENTS

| | | | |
|---|---|---|---|
| 3,699,950 A | 10/1972 | Humphrey, Jr. et al. ...... 128/23 |
| 4,693,244 A | 9/1987 | Daikuzono ............... 128/303.1 |
| 4,736,743 A | * 4/1988 | Daikuzono ............... 128/303.1 |
| 4,738,667 A | 4/1988 | Galloway .................... 604/281 |
| 4,832,979 A | 5/1989 | Hoshino ....................... 427/38 |
| 4,846,171 A | * 7/1989 | Kauphusman et al. ......... 606/15 |
| 4,923,268 A | 5/1990 | Xu ........................... 350/96.15 |
| 4,973,848 A | 11/1990 | Kolobanov et al. ....... 250/458.1 |
| 5,041,109 A | 8/1991 | Abela .......................... 606/15 |
| 5,061,265 A | 10/1991 | Abela et al. .................... 606/7 |
| 5,125,926 A | * 6/1992 | Rudko et al. ................. 606/19 |
| 5,129,897 A | 7/1992 | Daikunzono ................. 606/16 |
| 5,139,495 A | * 8/1992 | Daikuzono ................... 606/17 |

(List continued on next page.)

FOREIGN PATENT DOCUMENTS

| | | |
|---|---|---|
| EP | 0 583 921 A1 | 2/1994 |
| WO | WO 99/04709 | 2/1999 |
| WO | WO 99/15237 | 4/1999 |
| WO | WO 99/38445 | 8/1999 |
| WO | WO 99/48773 | 9/1999 |
| WO | WO 99/49926 | 10/1999 |

OTHER PUBLICATIONS

Copy of International Search Report PCT/US01/07088.
Indigo® "Diffuser–Tip™ Fiberoptics".

(List continued on next page.)

Primary Examiner—Michael Peffley
(74) Attorney, Agent, or Firm—Fish & Richardson P.C.

(57) ABSTRACT

A myocardial revascularization system that includes a laser energy source (e.g., a semiconductor laser), an outer guide member providing access to a patient's heart, and an optical fiber. The optical fiber is coupled to receive laser energy pulses from the source, is slidably located within the guide member, and is extendible from the distal end of the guide member. A drive motor is connected to the fiber to automatically move the distal end of the optical fiber with respect to the distal end of the guide member. A controller controls the drive motor to automatically move the fiber in synchronism with firing of the laser energy, and automatically calibrates the position of the distal end of the fiber with respect to the distal end of the catheter. The fiber has, at its tip, an enlarged portion with a front surface coated with a heat absorbing material that is nonmetallic and is partially transparent to the pulses. The outer guide member is 7 French or smaller and has a deflectable distal end. A lubricant is located between the optical fiber and an inner lumen surface of the guide member and on the outer surface of the outer guide member. Position sensing components are carried by the optical fiber and outer guide member at or near their distal ends.

4 Claims, 7 Drawing Sheets

U.S. PATENT DOCUMENTS

| | | | |
|---|---|---|---|
| 5,152,277 A | * 10/1992 | Honda et al. | 128/4 |
| 5,159,400 A | 10/1992 | Takeda et al. | 356/73.1 |
| 5,169,396 A | 12/1992 | Dowlatshahi et al. | 606/15 |
| 5,209,748 A | * 5/1993 | Daikuzono | 606/15 |
| 5,222,953 A | 6/1993 | Dowlatshahi | 606/15 |
| 5,282,472 A | 2/1994 | Companion et al. | 128/662.06 |
| 5,282,798 A | * 2/1994 | Bruse et al. | 606/17 |
| 5,306,274 A | * 4/1994 | Long | 606/15 |
| 5,320,620 A | 6/1994 | Long et al. | 606/28 |
| 5,348,552 A | * 9/1994 | Nakajima et al. | 606/13 |
| 5,359,192 A | 10/1994 | Williams et al. | 250/227.23 |
| 5,389,096 A | 2/1995 | Aita et al. | 606/15 |
| 5,409,483 A | 4/1995 | Campbell et al. | 606/15 |
| 5,415,655 A | 5/1995 | Fuller et al. | 606/16 |
| 5,464,404 A | 11/1995 | Abela et al. | 606/15 |
| 5,507,802 A | 4/1996 | Imran | 607/128 |
| 5,534,000 A | 7/1996 | Bruce | 606/15 |
| 5,549,600 A | 8/1996 | Cho | 606/15 |
| 5,607,421 A | 3/1997 | Jeevanandam et al. | 606/15 |
| 5,620,439 A | 4/1997 | Abela et al. | 606/11 |
| 5,695,493 A | 12/1997 | Nakajima et al. | 606/13 |
| 5,716,322 A | 2/1998 | Hui et al. | 600/133 |
| 5,725,521 A | 3/1998 | Meuller | 606/7 |
| 5,728,091 A | * 3/1998 | Payne et al. | 606/15 |
| 5,741,249 A | 4/1998 | Moss et al. | 606/33 |
| 5,742,718 A | 4/1998 | Harman et al. | 385/53 |
| 5,755,714 A | * 5/1998 | Murphy-Chutorian | 606/15 |
| 5,766,164 A | 6/1998 | Mueller et al. | 606/15 |
| 5,769,843 A | * 6/1998 | Abela et al. | 606/10 |
| 5,807,383 A | * 9/1998 | Kolesa et al. | 606/7 |
| 5,807,388 A | 9/1998 | Jeevanandam et al. | 606/15 |
| 5,824,005 A | * 10/1998 | Motamedi et al. | 606/15 |
| 5,832,929 A | 11/1998 | Rudko et al. | 128/898 |
| 5,871,495 A | 2/1999 | Mueller | 606/185 |
| 5,876,373 A | 3/1999 | Giba et al. | 604/95 |
| 5,891,133 A | 4/1999 | Murphy-Chutorian | 606/7 |
| 5,897,529 A | 4/1999 | Ponzi | 604/95 |
| 5,902,282 A | * 5/1999 | Balbierz | 604/264 |
| 5,913,853 A | 6/1999 | Loeb et al. | 606/15 |
| 5,925,012 A | 7/1999 | Murphy-Chutorian et al. | 604/30 |
| 5,951,541 A | 9/1999 | Simpson et al. | 606/7 |
| 5,951,543 A | 9/1999 | Brauer | 606/10 |
| 5,951,567 A | 9/1999 | Javier, Jr. et al. | 606/108 |
| 5,951,581 A | 9/1999 | Saadat et al. | 606/170 |
| 5,957,916 A | * 9/1999 | Jeevanandam et al. | 606/15 |
| 5,968,038 A | 10/1999 | Djeu | 606/16 |
| 5,972,012 A | 10/1999 | Ream et al. | 606/170 |
| 5,980,545 A | 11/1999 | Pacala et al. | 606/170 |
| 5,989,245 A | 11/1999 | Prescott | 606/14 |
| 5,989,278 A | 11/1999 | Mueller | 606/180 |
| 5,997,525 A | 12/1999 | March et al. | 604/508 |
| 5,997,531 A | 12/1999 | Loeb et al. | 606/13 |
| 5,999,678 A | 12/1999 | Murphy-Chutorian et al. | 385/117 |
| 6,001,091 A | 12/1999 | Murphy-Chutorian et al. | 606/1 |
| 6,171,303 B1 | * 1/2001 | Ben-Haim et al. | 606/15 |

OTHER PUBLICATIONS

Delivering The Promise, "Announcing The Family Of 2.5mm Laserprobes".

Eric Rosenthal et al., "Laser Thermal Angioplasty Probe ("Hot Tip") Temperature: Effect of Flow"; Lasers in Surgery and Medicine 10:124–132 (1990).

RM Verdaasdonk et al., Optically modified fiber tips penetrate tissue only when 'dirty', SPIE vol. 1201 Optical Fibers in Medicine V (1990), p. 129–136.

Rudolf M. Verdaasdonk, Ph.D., et al., "Modified Fiber Tips for Laser Angioplasty: Mechanisms of Action", Journal of Interventional Cardiology, vol. 3, No. 4, 1990, p. 243–253.

Ashley J. Welch, "The Thermal Response of Laser Irradiated Tissue", ©1984 IEEE.

Vera Russo et al., Lens–ended fibers for medical applications: a new fabrication technique, Oct. 1, 1984, vol. 23, No. 19, Applied Optics, p. 3277–3283.

RM Verdaasdonk et al., Explosive onset of continuous wave laser tissue ablation, Phys. Med. Biol., 1990, vol. 35, No. 8, 1129–1144, Printed in the UK.

Cardiodyne, The Cardiodyne™ Angiogenic Injection and Laser TMR System, Copyright 1998.

* cited by examiner

MYOCARDIAL REVASCULARIZATION

This application is a Division of application Ser. No. 09/519,502, filed on Mar. 6, 2000, now U.S. Pat. No. 6,464,693.

The invention relates to a system for performing myocardial revascularization on a beating heart of a patient.

Transmyocardial revascularization (TMR) is a surgical treatment for cardiovascular disease. Present TMR procedure uses a laser beam to drill holes of approximately 1 mm diameter through the myocardium, typically into the left ventricle. These holes or channels extend through the entire heart wall thickness from the outside through to the ventricle. The openings of the channels on the outside surface of the heart heal due to external pressure from the surgeon, but the channels remain open on the inside, allowing blood to enter the heart wall tissue from the ventricle.

In another approach myocardial revascularization can be performed using a catheter introduced percutaneously so that the tip of the catheter is inside a chamber of the heart, typically the left ventricle, where the holes or channels can be created from the inside toward but not through the outside of the heart. This approach is also known as endocardial laser revascularization (ELR), percutaneous myocardial revascularization (PMR), and direct myocardial revascularization (DMR). The channels are drilled with a laser beam introduced through the catheter. The catheter typically is an 8-French or 9-French catheter.

Certain problems are presented when laser revascularization is done on a beating heart. A beating heart presents a moving target, which can make it difficult to accurately and consistently form channels of a desired depth and size. The heart also is extremely sensitive to a laser pulse at certain times during its cycle. A laser pulse striking the heart during the T wave of the heart beat cycle could cause the heart to fibrillate and result in complications. While one could stop the heart during the process of TMR, this poses other risks to the patient and complicates the operating procedure. The heart must be cooled and the patient connected to a heart-lung machine.

However, the risk of inducing a beating heart to fibrillate is greatly reduced when the laser is fired only during the refractory period of the heart cycle between the R and T waves of the ECG signal. An additional benefit of firing the laser only between the R and T waves is that this is the period of the heartbeat cycle during which the heart is most still and channels can be formed most accurately. Rudko U.S. Pat. No. 5,125,926 describes a heart-synchronized pulsed laser system that fires a laser only during the refractory period of the heartbeat cycle. The patent describes an open chest procedure using an articulated optical arm or a fiber optic element to deliver the laser beam to a surface of the heart.

Aita U.S. Pat. No. 5,389,096 discloses a percutaneous myocardial revascularization procedure in which a steerable heart catheter is guided from the femoral artery via the abdominal artery into the left ventricle. The laser energy is delivered through the working channel of the catheter by a fiber optic delivery system.

SUMMARY OF THE INVENTION

In one aspect, the invention features, in general, a myocardial revascularization system that includes a laser energy source, an outer guide member providing access to a patient's heart, and an optical fiber. The optical fiber is coupled to receive laser energy pulses from the source, is slidably located within the guide member, and is extendible from the distal end of the guide member. A drive motor is connected to the fiber to automatically move the distal end of the optical fiber with respect to the distal end of the guide member. A controller controls the drive motor to automatically move the fiber in synchronism with firing of the laser energy.

In another aspect, the invention features, in general, a myocardial revascularization system that includes a laser energy source, an outer guide member providing access to a patient's heart, an optical fiber that is slidably located within the guide member, and a drive motor connected to the fiber to automatically move the distal end of the optical fiber with respect to the distal end of the guide member. A controller controls the drive motor and automatically calibrates the position of the distal end of the fiber with respect to the distal end of the catheter.

In another aspect, the invention features, in general, a myocardial revascularization system that includes a semiconductor laser energy source (e.g., a diode laser) that outputs laser pulses having a wavelength between 600 nm and 1000 nm, an optical fiber that is coupled to receive laser energy pulses from the source and to deliver them to a patient's heart tissue to be revascularized, and an outer guide member that engages the fiber and permits an operator to direct the tip to contact the patient's heart tissue to be revascularized.

In another aspect, the invention features, in general, a myocardial revascularization system that includes a laser energy source, an optical fiber that is coupled to receive laser energy pulses from the source and to deliver them to a patient's heart tissue to be revascularized, and an outer guide member that engages the fiber and permits an operator to direct the tip to contact the patient's heart tissue to be revascularized. The fiber has, at its tip, a heat absorbing material that is nonmetallic and is partially transparent to the pulses.

In another aspect, the invention features, in general, a myocardial revascularization system that includes a laser energy source, an optical fiber that is coupled to receive laser energy pulses from the source and to deliver them to a patient's heart tissue to be revascularized, and an outer guide member that engages the fiber and permits an operator to direct the tip to contact the patient's heart tissue to be revascularized. The fiber has an enlargened portion at the tip thereof that has a transverse dimension that is larger than the fiber diameter.

In another aspect, the invention features, in general, a myocardial revascularization system that includes a laser energy source, an outer guide member providing access to a patient's heart, and an optical fiber that is coupled to receive laser energy pulses from the source and is slidably located within the outer guide member. The outer guide member is 7 French or smaller and has a deflectable distal end that is deflectable by an operator-controlled mechanism.

In another aspect, the invention features, in general, a myocardial revascularization system that includes a laser energy source, an outer guide member providing access to a patient's heart, and an optical fiber that is coupled to receive laser energy pulses from the source and is slidably located within the outer guide member. A lubricant is located between the optical fiber and an inner lumen surface of the guide member.

In another aspect, the invention features, in general, a myocardial revascularization system that includes a laser energy source, an outer guide member providing access to a patient's heart, and an optical fiber that is coupled to receive laser energy pulses from the source and is slidably located within the outer guide member. A first position sensing component is carried by the optical fiber at or near the distal end of the fiber, and a second position sensing component is carried by the guide member at or near the distal end of the guide member.

In another aspect, the invention features, in general, a myocardial revascularization system that includes a laser energy source, an outer guide member providing access to a patient's heart, and an optical fiber that is coupled to receive laser energy pulses from the source and is slidably located within the outer guide member. The guide member has a distal end having a non-slip structure for engaging a surface location of a patient's heart tissue.

In another aspect, the invention features, in general, a percutaneous myocardial revascularization system that includes a laser energy source, a catheter for percutaneous access to a patient's heart, an optical fiber that is coupled to receive laser energy pulses from the source and is slidably located within the catheter. An inflation balloon is carried on the catheter at the distal end so as to prevent piercing the heart tissue of the patient with the catheter.

In another aspect, the invention features, in general, a percutaneous myocardial revascularization system that includes a laser energy source, a catheter for percutaneous access to a patient's heart, an optical fiber that is coupled to receive laser energy pulses from the source and is slidably located within the catheter, and a lubricant on the outer surface of the catheter.

Particular embodiments of the invention may include one or more of the following features. The fiber can be automatically advanced by the drive motor. The controller can receive signals indicating the patient's heart beat cycle (e.g., ECG signals) and synchronize laser firing and fiber movement to the patient's heart beat cycle. The fiber can be advanced after a short delay after initiation of firing of the laser. The laser firing can be synchronized to occur after the R wave of an ECG signal and to end at a time before the T wave. Alternatively, the laser firing can be synchronized to begin after the T wave and to end at a time before the next T wave.

In particular embodiments, the distal end of the outer guide member can be deflectable to varying amounts of tip deflection (e.g., up to 90 degrees or 120 degrees); a sensor can sense the extent of deflection and generate a signal indicating the extent of deflection, and the controller can receive the signal indicating the extent of deflection and determine a calibration adjustment for the position of the distal end of the fiber with respect to the distal end of the guide member as a function of the guide member deflection.

In particular embodiments, the controller can use the calibration adjustment to cause the fiber tip to be moved to an initialized position (e.g., about 1 mm) prior to firing the laser. The controller can fire the laser after moving fiber to the initialized position, and the receiving a fire signal from the operator. The controller can fire the laser after receiving an ECG signal after receiving the fire signal. The controller can advance the fiber after a delay of about 50 ms after initiating firing of the laser. The controller can advance the fiber a predetermined distance (e.g., at least 4 mm or at least 10 mm) in a predetermined period (e.g., less than 300 ms, though it can be greater than 300 ms) while continuing to fire the laser. The predetermined period can start after the R wave and end before the T wave. Alternatively, the predetermined period can start after the T wave and end before the next T wave. The predetermined period can be contained within one heart beat cycle or within more than one heart beat cycle. The predetermined period can include a period before the T wave and a period after the T wave wherein the laser is not fired and the fiber is not advanced during the T wave.

In particular embodiments, the controller can retract the fiber after discontinuing firing of the laser. The controller can cause the laser to fire a burst of energy as the fiber is being removed from the channel to coagulate the entrance to the channel in (TMR applications).

In particular embodiments, the drive motor used to move the fiber can be a stepper motor. The stepper motor can cause a fiber engagement member that engages a portion of the fiber external of the patient to be moved with respect to the outer guide member. The fiber engagement member can be moved by the stepper motor with respect to a handle to which the outer guide member is attached. A sheathed cable can be connected between the stepper motor and the handle. The sheathed cable can include an outer sheath that is secured to the fiber engagement member and an internal cable that is connected to the handle, such that, retraction of the internal cable within the outer sheath by the stepper motor causes the fiber engagement member to be moved toward the handle and the fiber to advance within the outer guide member.

In particular embodiments, the system can include a drug delivery system that delivers drugs from the distal end of the catheter in response to a drug delivery signal, and the controller can control the drive mechanism to move the fiber in synchronism with delivery of the drugs from the distal end of the catheter. Drug delivery can be synchronized to occur during movement of the distal end of the fiber away from the patient's heart tissue. The drug delivery can be synchronized to occur as the distal end of the fiber is removed from a channel formed in the heart tissue.

In particular embodiments, energy absorbing material can be located in a coating at an end surface portion of the fiber tip and not at a lateral surface portion of the tip. The energy absorbing material can include a coating of energy absorbing glass. The energy absorbing glass can be a coating of an optical glass filter that absorbs radiation at the wavelength of the laser energy source. The coating can include ionically colored glass. The coating can be about 20–30 um thick. The energy absorbing material can include carbon. The energy absorbing material can include metallic particles in nonmetallic material, e.g., glass. The fiber can be made of silica glass material. The coating can absorb between 5 and 40% (preferably between 15 and 25%) of the radiation directed to it.

In particular embodiments, the fiber tip can have an enlargened portion that has a transverse dimension of greater than about 600 um (e.g., about 700 um), and the fiber diameter can be less than about 500 um (e.g., about 400 um). The enlargened portion can be generally spherical. The enlargened portion can be made by heating the fiber, and the fiber can be made of material selected to have a surface tension so as to provide a 700 um tip dimension in a transverse direction. A lifeline can be attached to the enlargened portion to retain the enlargened portion in the event that it becomes separated from the fiber. The tip can include a material having a different refractive index than the material of the fiber, and a sensor can be used to monitor reflection returned from the interface of the material of the fiber and the material having a different refractive index to thereby confirm that the enlargened portion remains connected to the fiber.

In a particular percutaneous embodiment, the catheter can be 6 French or smaller. The catheter can have a fluoropolymer heat shrink tube over the optical fiber. The optical fiber can have a core diameter less than 800 um (preferably less than 500 um, e.g., about 400 um).

In embodiments employing a lubricant, the lubricant can be provided by a coating that creates a water film when exposed to an aqueous solution. The coating can be a water or solvent based hydrogel.

In embodiments employing position sensing components on the end of the fiber and outer guide member, the first position sensing component can be a magnetic material, and the second position sensing component can be a magnetic position sensor, e.g., a Hall effect sensor. Alternatively, the first and second position sensing components can be radiopaque markers.

Other advantages and features of the invention will be apparent from the following description of particular embodiments and from the claims.

DETAILED DESCRIPTION OF PARTICULAR EMBODIMENTS

Figure 1:
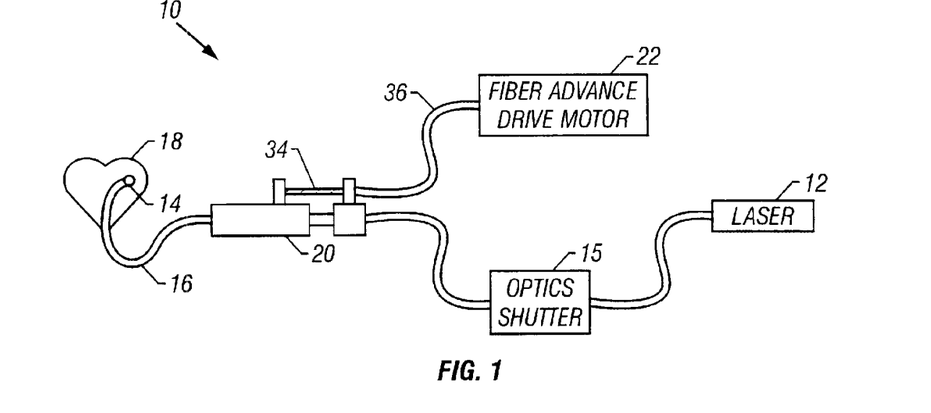
FIG. 1 is a diagram of a PMR system according to the invention.

Referring to FIG. 1, there is shown PMR system 10 for delivering laser energy from laser source 12 through an optic fiber 14 in catheter 16 to a patient's heart 18. PMR system 10 also includes a handle 20 that is engaged by the operator and an optional fiber advance motor 22 for automatically extending optic fiber 14 and a optics/shutter module 15 for controlling the laser energy delivered through optic fiber 14.

Figure 2:
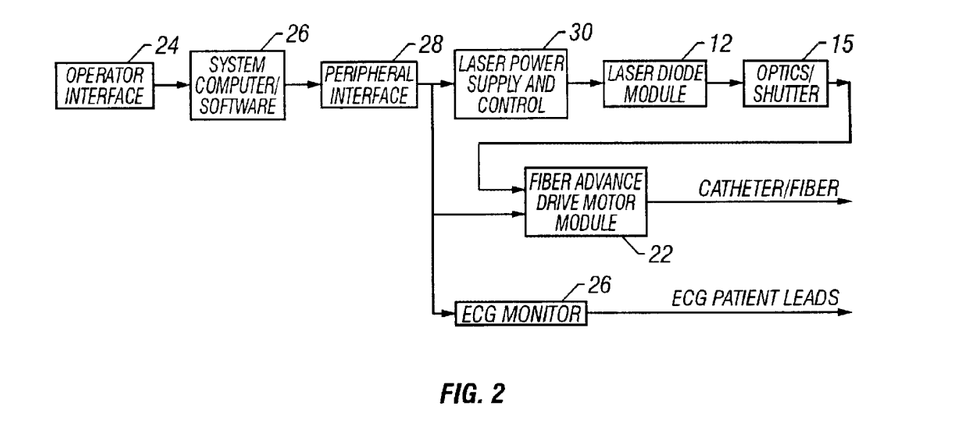
FIG. 2 is a block diagram of the functional subsystems of the FIG. 1 system.

Referring to FIG. 2, the functional components of system 10 are shown. They include Operator Interface 24, System Computer/Software 26, System Peripheral Interface 28, Laser Power Supply and Control 30, Laser Diode Module 12, Optics/Shutter 15, Fiber Advance Drive Motor Module 22, and ECG Monitor 26.

Operator Interface 24 allows control and monitoring of the system parameters. It consists of an electronic display and data entry panel. Operator controls include Laser ON/OFF, Laser ARM/DISARM and ECG Lead selection. The display displays laser energy, laser pulse Delay Time and ECG wave.

In System Computer/Software 26, the system computer runs the software, which controls and monitors all PMR functions. The computer is based on the x86 uniprocessor architecture, which runs DOS 6.2 or later. The System software is DOS based written in C language. C++ or other languages could also be used. The software includes a 1-millisecond interrupt loop to handle time critical processing.

The Peripheral Interface 28 is a circuit that translates all computer command signals to levels appropriate to the PMR subsystem devices.

The Laser Power Supply/Control 30 provides the standby and operating power for the laser diode. The power supply is initially turned on to supply the laser diode threshold (not lasing) current and then pulsed to supply current required for sufficient laser power to create tissue ablation.

The Laser Diode module 12 consists of an appropriately rated (e.g., 25 W) laser diode and a system for providing cooling to maintain the diode at the preferred operating temperature. (See FIG. 4.) The optics/shutter module 15 conditions the laser beam for entry into the fiber 14 housed in the catheter 16 and prevents unwanted laser energy delivery. It employs an electromechanical shutter and verifies the amount of energy being delivered. The output of the laser module is interrupted by the electromechanical shutter, which must be activated to allow laser energy delivery. The shutter normally reflects the laser energy onto an energy-measuring sensor while in the deactivated state. When the shutter is activated and opened, the laser beam is allowed into the launch optic coupling lenses, which condition the beam for entry into fiber 14.

The fiber advance drive motor module 22 (shown in more detail in FIG. 3) is used to pre-position the fiber tip (distal end), advance it at a programmed rate to a programmed distance, and then retract the fiber tip.

The ECG Monitor 26 is used to sense the patient ECG electrical activities and provide a suitable electronic representation for display. The monitor also processes the sensed electrical activity and provides a suitable indication when the peak of the R-Wave is occurring for use in synchronizing laser firing, fiber advancement and retraction, and optional drug delivery.

Figure 3:
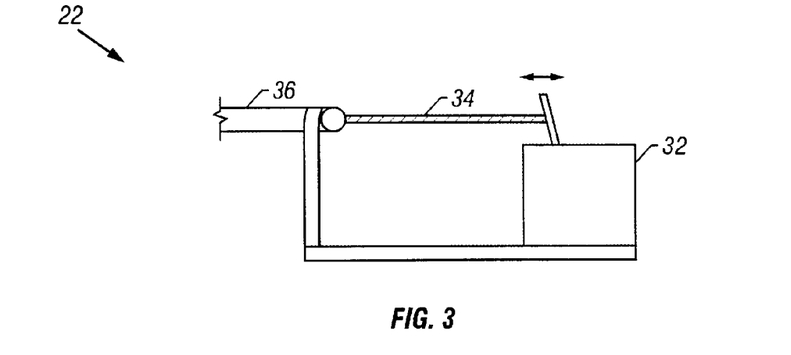
FIG. 3 is a perspective view of a fiber advance drive motor module of the FIG. 1 system.

Referring to FIGS. 1 and 3, fiber advance drive module 22 includes stepper motor 32, which moves internal cable 34 forward and backward with respect to outer sheath 36 in response to instructions from computer 26.

Figure 4:
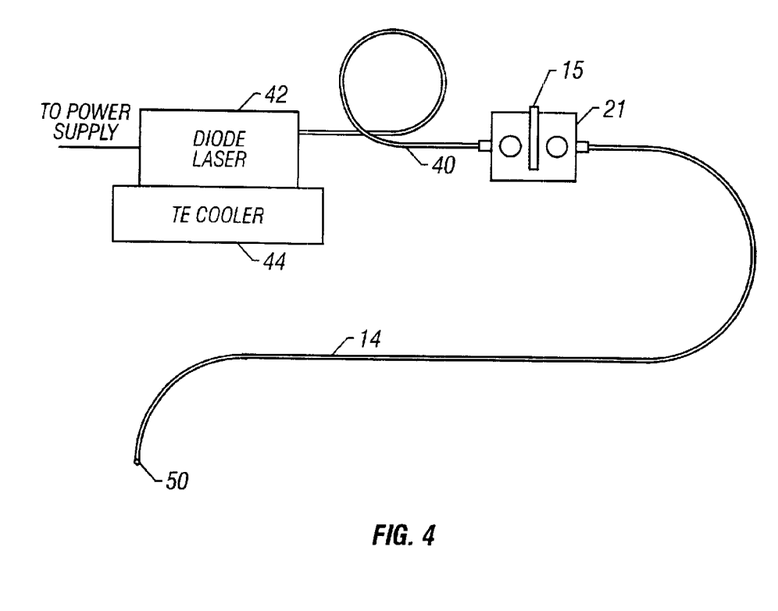
FIG. 4 is a diagram of the optic fiber circuit of the FIG. 1 system.
Figure 5:
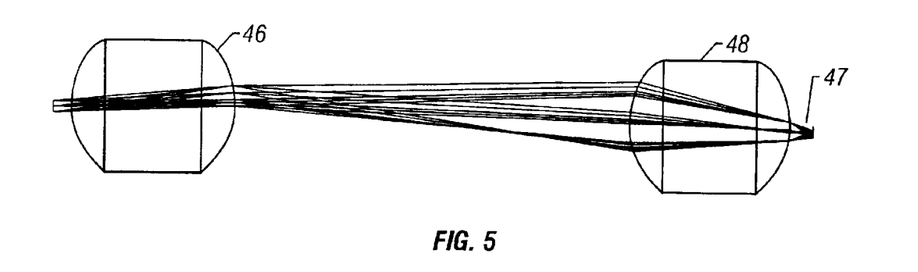
FIG. 5 is a diagram of the optics used in an optics/shutter module of the FIG. 1 system.

Referring to FIG. 4, it is seen that optical fiber 14 is connected through optics/shutter 15 to optic fiber 40 to diode laser 42 of laser module 12. Laser diode 42 is an 808-nanometer 25-watt semiconductor laser. Alternatively, other lasers operating at different wavelengths can be employed, e.g., other semiconductor lasers operating between 600 nm and 1000 nm. Module 12 also includes thermoelectric cooler 44 having Peltier elements that are modulated to maintain a set temperature. Optics/shutter module 15 also includes lens 46 and lens 48 (FIG. 5) to collimate the light from the 600 um core diameter of fiber 40 to the light going through the smaller 400 um core diameter of optical fiber 14 at 47. Other diameter fibers can be used; e.g., 400 um core diameter fibers could be used for both fiber 14 and fiber 40.

Figure 6:
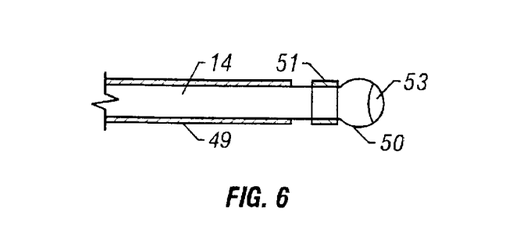
FIG. 6 is an elevation of the end of an optic fiber of the FIG. 1 system.

Referring to FIG. 6, optical fiber 14 includes a high numerical aperture (0.48NA), hard clad multimode 400 micron silica core with regular OH content available from 3M under the FT-400-URT product designation. The fiber cladding and buffer coating are polymer based. The high NA fiber provides for minimal optical losses when the energy is launched into the fiber core. Optical fiber 14 preferably includes a PTFE fluoropolymer shrink tube 49 over the outer diameter of the fiber jacket to reduce the coefficient of friction during fiber advance through the catheter. The jacket also increases the column stiffness of the fiber assembly to minimize fiber backlash when the fiber assembly is retracted in the catheter. A lubricant, preferably a hydrogel, can also be provided on the outer surface of fiber 14. The hydrogel is activated in an aqueous environment and provides a thin film to reduce the coefficient of friction. The hydrogel can include a soluble material of polyvinyl pyrolidone that is bound to a polymer matrix. The hydrogel can be in a water-soluble liquid form, applied via dipping or spraying and UV cured. Alternatively the hydrogel may be solvent based and cured via heat. Other soluble materials include polyvinyl alcohol, polyethylene oxide, or polypropylene oxide.

Still referring to FIG. 6, enlarged portion 50, which is spherical in shape, is at the distal end of fiber 14. Enlarged portion 50 includes a thin coating 53 of an optical glass filter 20–30 microns thick. The optical glass filter is ionically colored glass available from Schott. The optical glass filter reduces the transmission of energy through the glass in the near IR and generates heat in the tip. Preferably the coating absorbs between 5 and 40%, most preferably around 20% of the radiation directed to it; as the percentage goes significantly above the optimal range, undue heat may be generated; as the percentage goes significantly below the optimal range, insufficient heat may be generated, or it may not be generated quickly enough.

Marker band 51 is attached to the fiber shaft at a distance of 0.215 inches from the spherical tip to create a radiopaque marker to line the fiber up with the catheter tip under fluoroscopy. This enables positioning of the fiber tip in relation to the catheter tip. Preferably the marker bands are non-metallic, to avoid concentrating energy from the fiber. Potential materials for the marker are tantalum and barium sulfate filled polymer.

Figure 7:
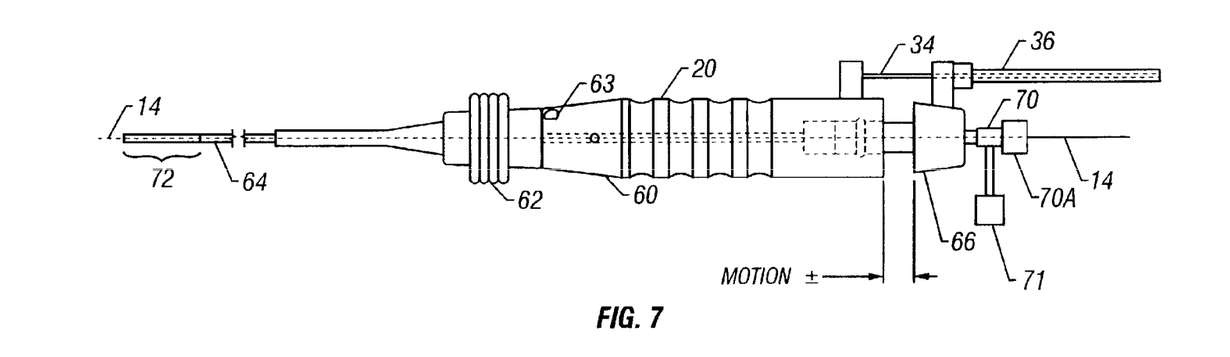
FIG. 7 is an elevation of a handle and attached components of the FIG. 1 system.
Figure 8A:
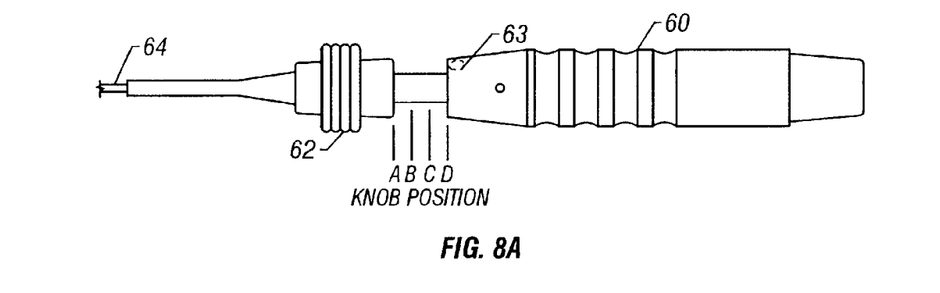
FIGS. 8A–8D show the end of the catheter of the FIG. 1 system in different bent positions.
Figure 8B:
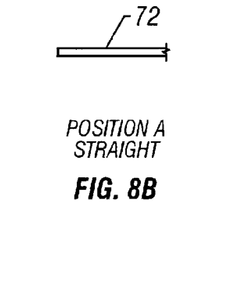
Figure 8C:
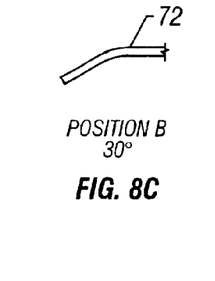
Figure 8D:
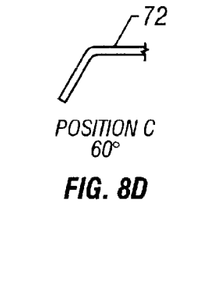
Figure 8E:
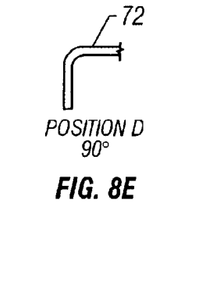
FIG. 8 is an elevation of the FIG. 7 handle shown in a different operative position.

Referring to FIG. 7, handle 20 includes a hand-engageable portion 60 and a catheter deflecting knob 62. Catheter 64 is connected at the front of hand-engageable portion 60, and fiber driver 66 is connected at the rear. Outer sheath 36 is connected to fiber driver 66 so that when cable 34 is retracted within sheath 36, fiber driver 66 and fiber 14 secured therein are advanced within handle 20. Fiber 14 is secured to driver 66 by a Toughy Borst fiber lock 70a. Hemostasis valve assembly 70 is used to deliver liquid inside of catheter 64 and seals against fiber 14. At the distal end of catheter 64 is a so-called "floppy section" 72 that is bent by operating deflecting knob 62.

Referring to FIG. 8, deflecting knob 62 is shown separated from hand engageable component 60. Four knob positions A, B, C, and D are shown in FIG. 8. These correspond to the positions shown in FIGS. 8A–8D. Sensor 63, in hand engageable portion 60, senses the position of knob 62 and thus the position of floppy section 72 and transmits it through appropriate wires to computer 26. In FIG. 8A, the floppy section 72 is straight in position A. In FIG. 8B, the floppy section 72 is shown bent to an angle of 30 degrees in position B. In FIG. 8C, the floppy section 72 is shown bent to an angle of 60 degrees in position C. In FIG. 8D, the floppy section 72 is shown bent to an angle of 90 degrees in position D.

Figure 9:
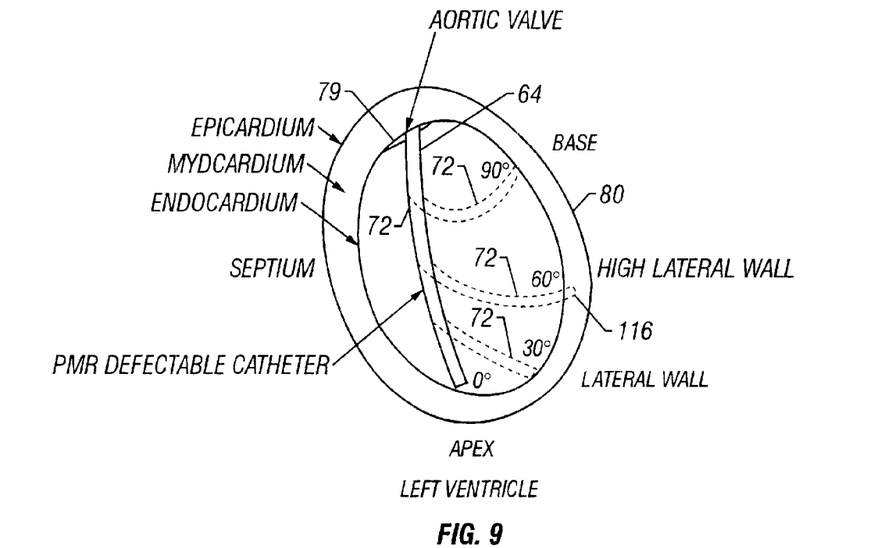
FIG. 9 is a diagram of the end of the catheter in different positions in the left ventricle of the patient's heart.

Referring to FIG. 9, catheter 64 is shown within left ventricle 80 of the patient's heart 18, with the floppy section 72 shown in four different positions such that it engages different locations of the heart wall. In the 0 degree position, the laser catheter contacts the apex. In the 30 degrees position, the laser catheter contacts the lateral wall. In the 60 degrees position, the catheter engages the high lateral wall. In the 90 degrees position, the catheter engages the base.

Figure 10:
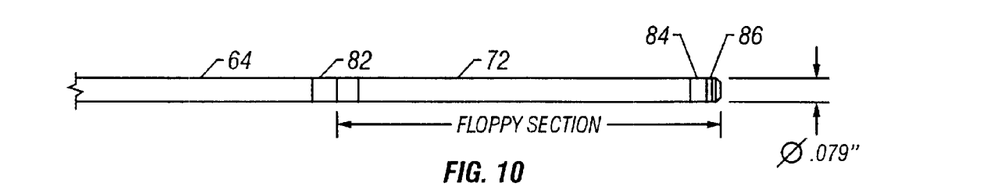
FIG. 10 is an elevation of the end of the FIG. 9 catheter.
Figures 11, 12:
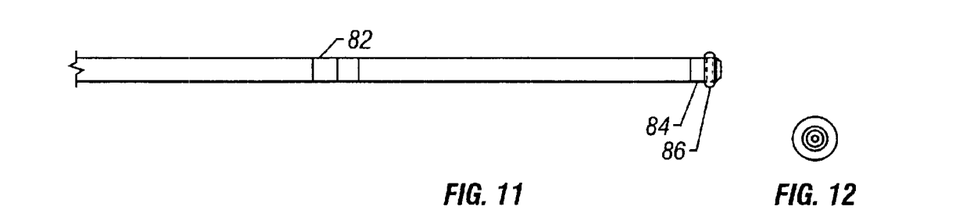
FIGS. 11 and 12 are an elevation and a side view of the FIG. 10 catheter with its balloon inflated.
Figure 13:
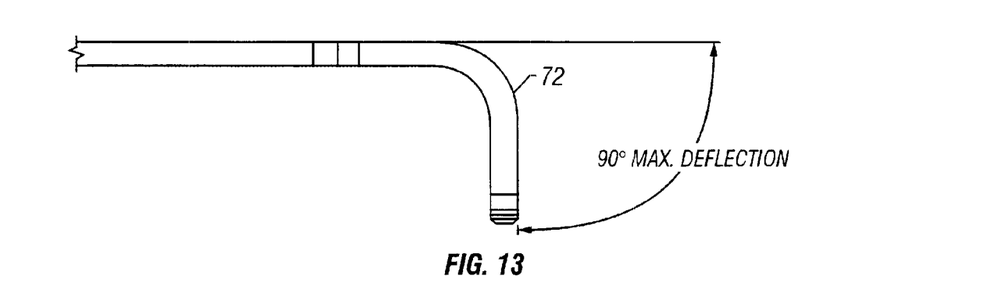
FIG. 13 is an elevation showing the FIG. 10 catheter in a bent orientation.

Referring to FIG. 10, catheter 64 has radiopaque markers 82, 84 (e.g., of gold or other suitable material) at the two ends of the floppy section 72. Catheter 64 also carries a balloon 86 at the distal end. In FIGS. 11 and 12, balloon 86 is shown inflated. In FIG. 13, floppy section 72 is shown bent 90 degrees. In this position, markers 82, 84 are in a different orientation than shown in FIGS. 10 and 11, and this would be seen on a fluoroscope in use.

Figure 14:
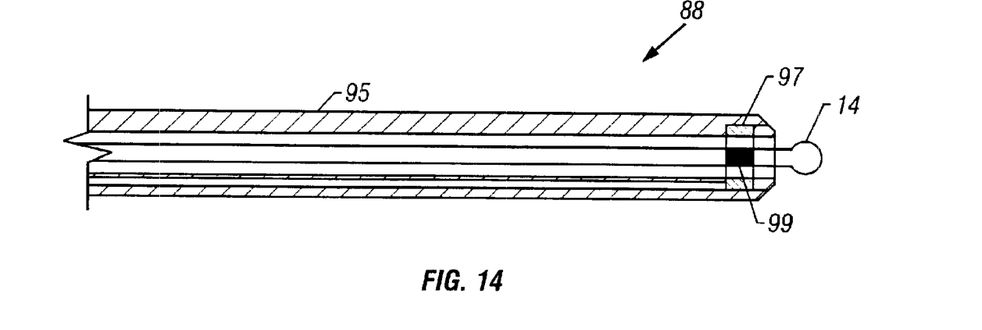
FIG. 14 is a vertical sectional view of an alternative catheter of the FIG. 1 system.

Referring to FIG. 14, an alternative catheter end 88 is shown. It includes a magnetic position sensor 97 within the catheter wall 95. Fiber 14 has a magnetic portion 99 at a known distance from the end of the fiber. Sensor 97 for example is a Hall effect sensor that can determine the relative position a magnetic portion 99 with respect to sensor 97.

Figure 15:
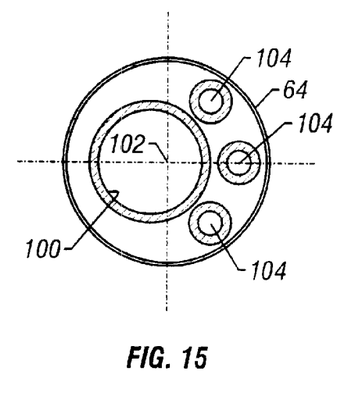
FIGS. 15 and 16 are vertical sectional views of different embodiments of the catheter used in the FIG. 1 system.
Figure 16:
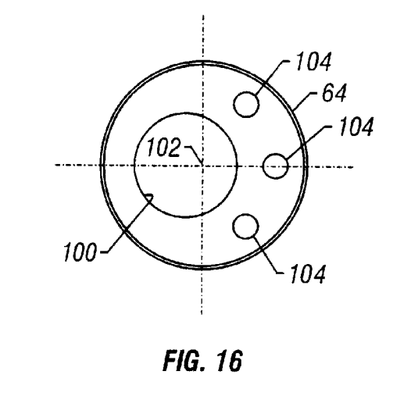

Referring to FIGS. 15 and 16, the cross-section of catheter 64 is shown. Catheter 64 has a large lumen 100 through which fiber 14 passes. This lumen is off center from the center 102 of the catheter 64. The catheter 64 also has three smaller lumens 104, used for a bending wire for floppy section 72, electrical wires for sensors, and/or drug delivery. In manufacture, catheter 64 is extruded with lumens 100 and 104. The lumens can be provided to the final desired size in the extruded material (FIG. 16), or can be provided by extruding holes at a larger size, and then inserting tubes having the desired inner diameters into the extruded holes (FIG. 15). The central lumen is 4.5 French, and the deflectable floppy tip is 6 cm long. Alternatively the lumen can be a different size, e.g., 3-French. The entire catheter shaft is 110 centimeters long. A control wire extends in one of lumens 104 through the catheter shaft to the tip of the floppy section 72. The distal end of the floppy section 72 is anchored to the catheter tip, and the proximal end is attached to the control wire connected to knob 62. The control handle knob 62 is retracted to place a bend in the floppy tip.

Figure 17:
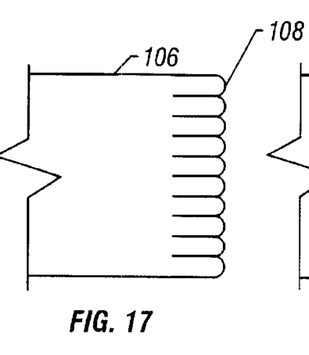
FIGS. 17–19 are diagrammatic elevations showing different embodiments for the end of the catheter of the FIG. 1 system.
Figure 18:
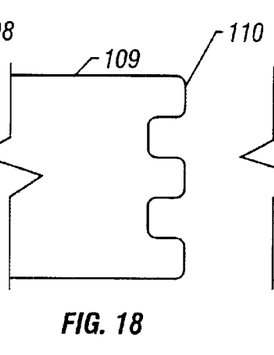
Figure 19:
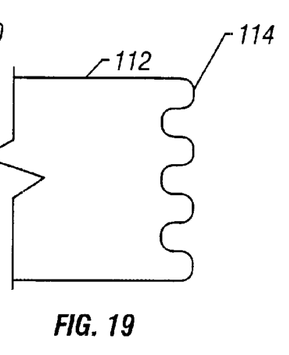

Referring to FIGS. 17–19, there are shown three alternative forms for the end of catheter 64. In FIG. 17, catheter end 106 has a plurality of slit bumps 108. In FIG. 18, catheter end 109 has a smaller number of larger, generally rectangular portions 110. In FIG. 19, catheter end 112 has curved protrusions 114 of an intermediate size.

In use, the medical professional, generally a cardiologist, places the end of catheter 64 into the appropriate location of the heart, generally the left ventricle, via the percutaneous technique. The six-French catheter size provides for multiple access points: femoral artery, radial artery, and corotoid artery. Access at a point other than the femoral artery enables the patient to be ambulatory in shorter period of time. First the guidewire is directed through the vasculature to the heart. The catheter 64 is then placed over the guidewire, which passes through large lumen 100, and directed over the guidewire to the heart. The distal end of catheter 64 passes through the aortic valve 79 into the left ventricle 80 (FIG. 9). The location of the delivery system and distal tip is visualized with a fluoroscope, using markers 82, 84. When the catheter is in the proper location, the guidewire is removed, and fiber 14 is fed through lumen 100.

The end of the fiber 14 is then calibrated relative to the end of catheter 64 for different angles of bend. The catheter is first placed with the floppy tip positioned straight (knob position A) within the left ventricle 80. The front edge of the radiopaque marker 51 on the fiber is lined up with the back edge of the catheter tip marker 84, and the fiber 14 is clamped at 66 at this position, and the position of stepper motor 32 at this time is recorded; the positions of stepper motor for knob positions B, C, and D (with marker 51 aligned with marker 84) can then be estimated. Thereafter, as the catheter tip is deflected, the fiber position is automatically adjusted by a feedback system from the catheter control knob sensor 63, to computer 26, to the fiber advance drive motor module 12. Alternatively, the fiber tip can be automatically positioned in relation to the catheter tip by utilizing the Hall effect sensor 97 for the FIG. 14 embodiment. When the magnetic portion lines up with the sensor, computer 26 records the position of stepper motor 32. Sensing the fiber tip location and adjusting it automatically ensures consistent channel depth at varying tip deflection.

Balloon 86 is then inflated to increase surface area of the catheter tip to reduce pressure applied by it at the heart wall and to prevent the tip of the catheter from piercing the heart wall. The tip of the catheter is positioned against the endocardial wall in the region to be treated, with the tabs or protrusions 108, 110, or 114 (FIGS. 17–19) providing a nonslip engagement with the wall. Saline solution is periodically injected via a syringe into the hemostasis valve side arm 71 and flushed through the catheter 64. The saline solution travels between the fiber outer diameter and inner lumen 100 of catheter 64 to the distal tip of the catheter 64. The flushing prevents blood clots, and debris from entering and sticking to the catheter tip and the fiber.

Figure 20:
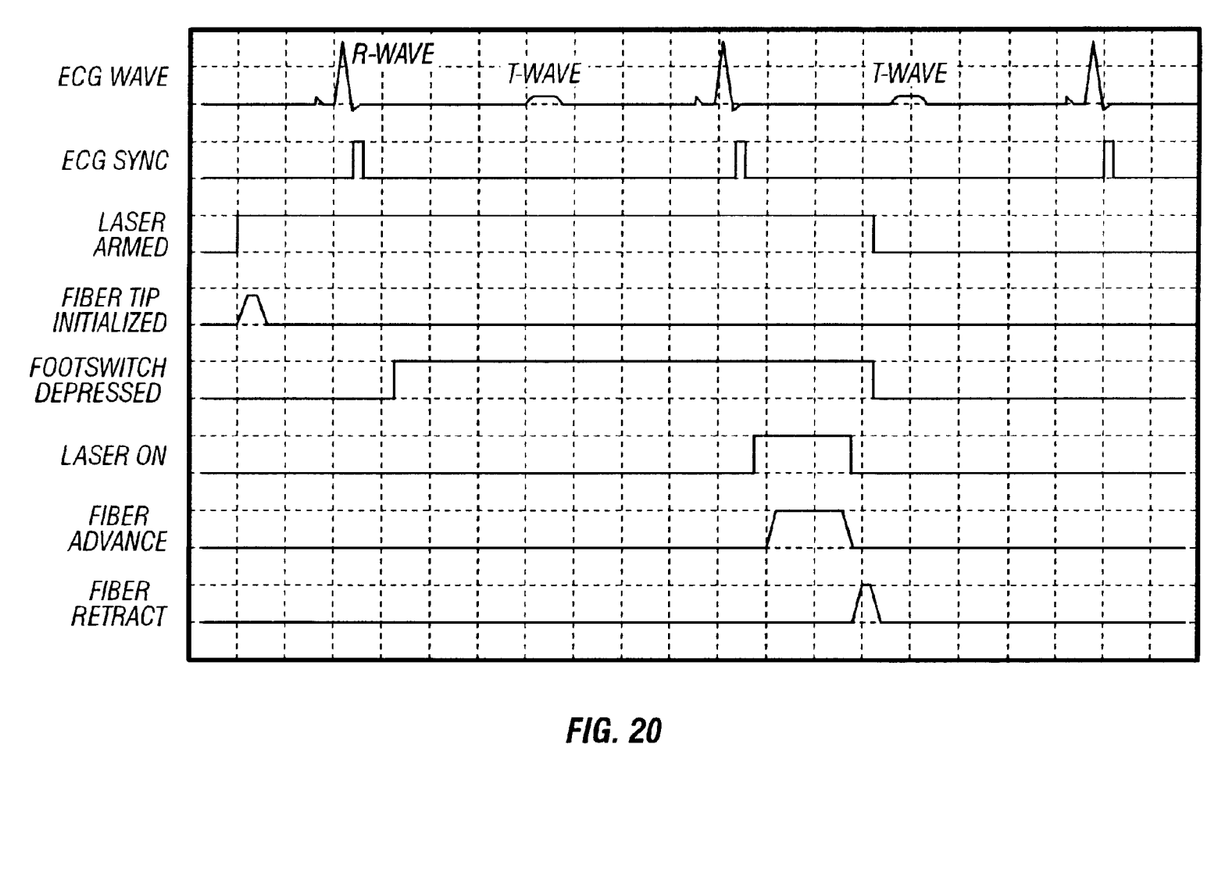
FIG. 20 is a diagram of the timing of the FIG. 1 system with respect to ECG, laser firing, and fiber advancement and retraction.

When the tip is in proper position at a location for creating a channel in the heart tissue, the fiber tip is automatically advanced until it is 1 mm past the catheter tip. The operator then steps on a foot pad switch (not shown) to cause automatic laser firing with fiber advancement and retraction, at the next appropriate time in the heart beat cycle, as is set forth in the timing diagram of FIG. 20. The laser pulse delivery sequence is initiated when the laser is armed (by providing an initial power level to laser 42) and the footswitch (not shown) is depressed. When these conditions are met, the first occurrence of the R-wave peak will initiate laser energy delivery and fiber advancement. The timing sequence is as follows: Each peak of the R-Wave generates an ECG SYNC, which the computer/software uses to initiate the laser pulse timing when the laser 42 is armed, the footswitch is depressed and all system safety functions are normal. Normally the fiber tip is protected inside the catheter. When the laser is armed, the tip is advanced to protrude 1 millimeter beyond the catheter tip to initialize the fiber tip 50 at the treatment position. At the next occurrence of the ECG SYNC (at the peak of the R-Wave) following laser arming and footswitch depression, the shutter in module 15 is opened, and the laser energy pulse is initiated. The fiber advancement is delayed a period of time (e.g., 50 ms) from the start of the laser pulse to allow preheating of the fiber tip (dwell), and is then advanced for 4 millimeters in a selected time (e.g., 260 ms or less); other times can be used. The end of the laser pulse disarms the laser, closes the shutter, and initiates fiber retraction. Fiber retraction time (e.g., 40 ms) is chosen to ensure that all channel formation activities are finished before the onset of the ECG T-Wave. Alternatively, the laser firing could start after the T wave and end before the following T wave.

The laser system forms a channel, e.g., channel 116 shown in FIG. 9, from the endocardial surface into the myocardium. The distance of advancement of the fiber establishes the depth of the channel, and the fiber tip size at enlarged portion 50 establishes the diameter of the channel. Firing the system transmits energy from the energy source 12, through the delivery system of fiber 40, optics 15, and fiber 14. A portion of the energy delivered to the fiber tip is absorbed by glass coating 53, where it is converted to heat. At the initiation of laser firing, coating 53 heats up and causes denaturing and carbonization of the heart tissue that it contacts. The radiation, at 808 nm, is not generally absorbed by heart tissue in its normal state. After heating the tissue, however, the tissue is converted to an absorbing state, and thereafter absorbs the laser energy that is transmitted through the tip of the fiber while the fiber is advanced, creating channel 116, approximately 5 mm deep, by the process of ablation.

The use of a larger tip diameter of enlargened portion 50 permits one to form a channel with a desired diameter that is larger than the base diameter of the fiber 14. This improves fiber flexibility, which provides improved navigation and resiliency in the human vasculature. During advancement of the fiber into the channel being created, vaporized tissue and blood created by the ablation can escape through a "vent" created by the reduction in diameter from the tip to the fiber shaft. The vapor passes into the left ventricle with PMR and into the atmosphere with TMR. The vent also prevents excess acoustical damage that can be caused by a straight fiber. Excess acoustical damage contributes to tissue tearing and cellular damage, which may adversely affect the intended function of the PMR/TMR channel.

Upon retraction of the fiber from the channel 116 (FIG. 9), drugs are optionally injected into the channel from the catheter tip to the site. Upon completion of channel formation, the balloon 86 is deflated, and the catheter returns to a 6-French profile.

After a channel has been created at one location, the delivery system is moved to the next location and the channel formation process is repeated until all the required channels are formed.

A hydrogel coating on the outer diameter of the catheter shaft provides ease of insertion of the device through the vasculature and improves maneuverability in the ventricle. During the procedure, lumen 100 is periodically flushed with sterile saline solution (0.90% sodium chloride in water) via valve sidearm 71. The flushing prevents blood clots from forming between the outer diameter of the fiber assembly and the inner lumen of the catheter, and the aqueous environment activates the hydrogel lubricant coated on the outer diameter of fiber 14, such that the coefficient of friction of the two surfaces is reduced by approximately a factor of 5–10 times. The lubricant promotes movement through lumen 100 in the feeding, bending (as floppy section 72 is bent), initialization of tip end, advancement and retraction phases of its movement.

System 10 minimizes any electrical stimulation to the heart by synchronizing laser firing to occur at a safe period in the heart beat cycle. The laser energy delivery is synchronized to begin after the peak of the patient ECG R-Wave and end before the occurrence of the T-Wave. Thus the laser energy is delivered for channel creation during the time in which the patient's heart is inactive and minimizes any electrical stimulation. Synchronizing the ablation to start with the R wave and end before the T-wave eliminates positive ventricular contractions (PVC's). Alternatively, the firing could be synchronized to the R wave (or other appropriate event) and begun after the T wave and ended before the next T wave.

Synchronizing the timing of fiber advance and laser power eliminates tissue tearing, and minimizes thermal, acoustical, and collateral damage in general. The system creates reproducible channels with minimal tissue damage. The use of a diode laser permits the system to be packaged in a compact housing on either side of an operating table from the cardiologist. The control panel allows the operator to set the depth to 1 mm or 5 mm, and the controller automatically sets the energy level, distance of travel, and time to achieve the set depth.

Drug delivery is achieved through the central catheter lumen or through a separate lumen in the catheter shaft.

Figure 21:
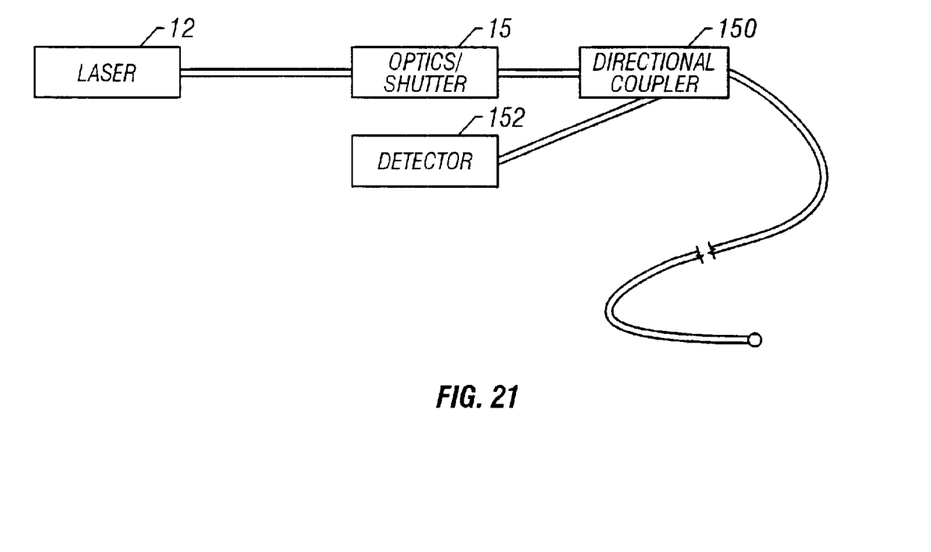
FIG. 21 is a diagram showing a system used to detect whether the end of the fiber has broken off.

Referring to FIG. 21, directional coupler 150 and detector 152 can be used to verify that enlarged portion 50 has not broken from fiber 14. The light from laser source 12 passes through fiber 14, and the change in refractive index at coating 53 causes some of the light to be reflected back towards the source. This light that is reflected is diverted at directional coupler 150 and detected at detector 152. If there is a change in reflected light, this is taken as an indication that the enlarged portion 50 has broken off from fiber 14.

Figure 22:
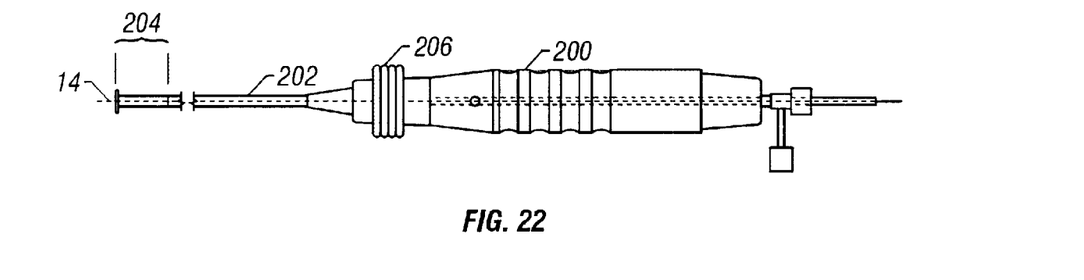
FIG. 22 is an elevation of a modified handle used in TMR.
Figure 23:
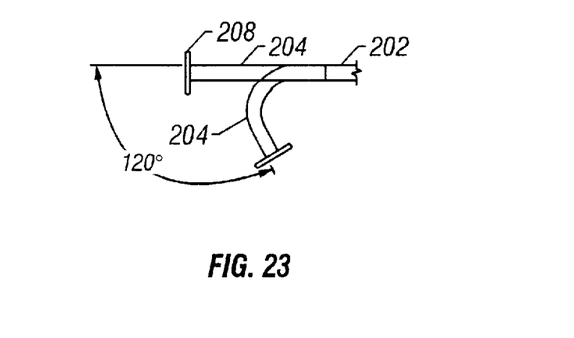
FIG. 23 is a view of an end section of a guide member of the FIG. 21 handle shown in different positions.

Referring to FIG. 22, TMR handle 200 is similar to PMR handle 20, and can be used with the subsystems shown in FIGS. 2–8 and 10–20 in a procedure in which the channels are created from the outside of the heart, as described for the particular embodiment of U.S. Pat. No. 5,125,926, which is hereby incorporated by reference. Thus the discussion of the structure and operation of system 10 with PMR handle 20 also applies to TMR handle 200, with the exception of the differences described here. The primary difference between TMR handle 200 and PMR handle 20 is that handle 200 has a 6–9 inch long, 10 French outer guide member 202 instead of 100 cm, 6-French catheter 64. Outer guide member 202 has a 3–4 cm long floppy section 204, that is controlled by deflecting knob 206 and can be deflected from 0 degree to 120 degrees. Flat end surface 208 is located at the end of outer guide member 202 and carries slip resistant surface features such as a pattern of protrusions (FIG. 23.) Also, laser 42 is a 50-watt laser.

In use, outer guide member 202 and optic fiber 14 inside are directed to the back side of the heart employing a minimally invasive thoracoscopic procedure involving a small port incision through the chest or a thoracotomy or a stemotomy. Flat end surface 208 can be remove or reduced in size when used thoracoscopically. Access to the heart can be via a thoracotomy when TMR is performed alone and via a sternotomy when TMR is performed in combination with coronary artery bypass grafting (CABG). The pericardium is excised in the traditional way prior to positioning the end 208 of outer guide member 202. Alternatively, the channel can be formed through the pericardium, with the opening to the channel at the epicardial surface being sealed by a laser burst as the fiber tip is removed from the channel.

The end 208 of outer guide member 202 is positioned against the wall in the region to be treated, with the cardiologist bending floppy section 204 as needed using deflecting knob 206. The system is armed and fired to form a channel from the epicardial surface through the myocardium to the interior of the left ventricle. The tip of fiber 14 is automatically advanced an appropriate distance (e.g., 10–15 mm) into the channel as it is created, and the fiber is automatically retracted after channel formation. The distance varies depending on the heart wall thickness; the distance is set to be longer than the thickness of the wall to guarantee that the channel passes all of the way through into the left ventricle. Drugs can be delivered through a lumen. The channel entrance site can be sealed via cauterization by an energy burst as the end of fiber 14 is removed from the mouth of the channel or via a sealant applied through a shaft lumen. The small profile enables delivery of energy with minimal manipulation. Channel formation can be confirmed using an imaging technology such as echocardiography. The control panel allows the operator to change the energy level in 1-Joule increments or a power level in 1-watt increments for TMR procedures; in particular, the user sets the desired channel depth, which varies depending on heart wall thickness, and the controller sets the proper energy level, distance of travel, and time. E.g., for a 10 mm thick wall, the distance of travel would be set at greater than 10 mm, e.g., 12 mm.

Laser diode 42 is a compact, inexpensive, high-power, controllable source of laser energy. While its 808 nanometer wavelength generally cannot be used to ablate heart tissue, by providing a partially absorbing tip coating, the tip is heated, to initially heat adjacent heart tissue to a state in which the tissue does absorb 808 nanometer energy.

The incorporation of an optical glass filter coated on a spherical silica fiber tip produces repetitive ablation (consistent channel formation) and minimal tissue damage (thermal and mechanical) in the blood tissue environment present in PMR or TMR. An advantage of the use of a transparent tip (as opposed, e.g., to a metal tip) is that the shaft of the fiber is not heated to a significant extent. This is due to lower thermal conductivity of the transparent material. Also, having the heat directed out the end of the fiber and not to the sides of the fiber, limits thermal damage to the tissue along the edge of the channels to a small depth (unlike some other procedures). This minimizes the thermal damage and amount of scar tissue formed in the channel. The minimal tissue damage promotes collateral vessel formation adjacent to the channel. This facilitates increased perfusion of blood in the myocardium.

Other embodiments of the invention are within the scope of the appended claims.

In addition to diode lasers, other semiconductor lasers can be used. Also, a 6-French catheter can be used within a guide catheter.

What is claimed is:

1. A myocardial revascularization system comprising
   a laser energy source,
   an outer guide member providing access to a patient's heart, said guide member having a distal end,
   an optical fiber that is coupled to receive laser energy pulses from said source and is slidably located within said guide ember, said fiber having a distal end that is extendible from said distal end of said guide member,
   a drive motor connected to said fiber to automatically move said distal end of said optical fiber with respect to said distal end of said guide member, and a controller that controls said drive motor to automatically move said fiber in synchronism with firing of said laser energy, further comprising a drug delivery system that delivers drugs from said distal end of said catheter in response to a drug delivery signal, and a controller that controls said drive mechanism to move said fiber in synchronism with delivery of said drugs from said distal end of said catheter.

2. The system of claim 1 wherein said controller causes said drive motor to advance said distal end of said fiber toward the patient's heart tissue and to retract said distal end of said fiber away from the patient's heart tissue, and wherein drug delivery is synchronized to occur during movement of said distal end of said fiber away from the patient's heart tissue.

3. The system of claim 2 wherein said drug delivery is synchronized to occur as said distal end of said fiber is removed from a channel formed in said heart tissue.

4. A myocardial revascularization system comprising a laser energy source, an an optical fiber that is coupled to receive laser energy pulses from said source and to deliver them to a patient's heart tissue to be revascularized, said fiber having a fiber diameter, said fiber having an enlarged portion at the tip thereof, said enlarged having a transverse dimension that is larger than said fiber diameter, and an outer guide member that engages said fiber and permits an operator to direct said tip to contact said patient's heart tissue to be revascularized, wherein said outer guide ember comprises a catheter for percutaneous access to said patient's heart, said catheter having a distal end adapted to be directed via said patient's vasculature into said patient's heart and a proximal end external of said patient's body, wherein said fiber is slidably located within said catheter, said fiber having a distal end that is extensible from said distal end of said catheter, said enlarged portion being on said distal end, further comprising a life-line attached to said enlarged portion to retain said enlarged portion in the event that it becomes separated from said fiber.

* * * * *